(12) United States Patent
Kalvinsh et al.

(10) Patent No.: US 7,223,797 B2
(45) Date of Patent: May 29, 2007

(54) MELDONIUM SALTS, METHOD OF THEIR PREPARATION AND PHARMACEUTICAL COMPOSITION ON THEIR BASIS

(75) Inventors: Ivars Kalvinsh, Ikshkile (LV); Anatolijs Birmans, Riga (LV)

(73) Assignee: Joint Stock Company "Grindeks", Riga (LV)

( * ) Notice: Subject to any disclaimer, the term of this patent is extended or adjusted under 35 U.S.C. 154(b) by 0 days.

(21) Appl. No.: 10/567,130

(22) PCT Filed: Jul. 15, 2004

(86) PCT No.: PCT/LV2004/000005

§ 371 (c)(1), (2), (4) Date: Feb. 7, 2006

(87) PCT Pub. No.: WO2005/012233

PCT Pub. Date: Feb. 10, 2005

(65) Prior Publication Data

US 2006/0264506 A1  Nov. 23, 2006

(30) Foreign Application Priority Data

Aug. 4, 2003  (LV) ..................................... P-03-87
Aug. 4, 2003  (LV) ..................................... P-03-88

(51) Int. Cl.
*A01N 37/30* (2006.01)
*A01N 37/00* (2006.01)
*C07C 205/00* (2006.01)
*A61K 47/44* (2006.01)

(52) U.S. Cl. ...................... 514/556; 504/320; 562/553; 424/316

(58) Field of Classification Search ................ 514/556; 504/320; 562/553; 424/316
See application file for complete search history.

(56) References Cited

U.S. PATENT DOCUMENTS 4,481,218 A   11/1984   Astapenok et al.
5,071,611 A   12/1991   Bremanis et al.

FOREIGN PATENT DOCUMENTS

WO   WO97/06795   2/1997

OTHER PUBLICATIONS

S. Ayushieva, et al., "Iodide trimethylhydrazinium propionate in experimental hepatitis", Database Chemabs, Database accession No. 2001:45205.
O.P. Il'Ina, et al., "Efficacy of iodide trimethylhydrazonium propionate in the case of thyroid gland hypofunction" Database Chemabs, Database accession No. 2000:710269.
G.K. Shutov, et al. "Regulating lupine growth", Database Chemabs, Database accession No. 1983:121372.
International Search Report for PCT/LV2004/000005, Mar. 7, 2005.
International Preliminary Report on Patentability for PCT/LV2004/000005, Mar. 2, 2005.

*Primary Examiner*—James Wilson
*Assistant Examiner*—MLouisa Lao
(74) *Attorney, Agent, or Firm*—Hueschen and Sage

(57) ABSTRACT

New salts of Meldonium, the method of their preparation, and pharmaceutical formulation on their basis have been described. The general formula of these salts is $X^-(CH_3)_3N^+NHCH_2CH_2COOH$ where $X^-$ is an acid anion selected from the group of pharmaceutically acceptable acids. Practically non-hygroscopic and/or increased thermal stability and/or lasting action Meldonium hydrogen salts of fumaric acid, phosphoric acid, oxalic acid, maleic acid, and pamoic acid as well as Meldonium orotate and galactarate are especially suitable. Novel pharmaceutical formulations containing non-hygroscopic and/or increased thermal stability and/or and/or lasting action 3-(2,2,2-trimethylhydrazinium) propionate salts for oral parenteral, rectal, and transdermal introduction are concurrently described.

14 Claims, No Drawings

MELDONIUM SALTS, METHOD OF THEIR PREPARATION AND PHARMACEUTICAL COMPOSITION ON THEIR BASIS

TECHNICAL FIELD

The present invention relates to 3-(2,2,2-trimethylhydrazinium)propionate salts of the general formula $X^-(CH_3)_3N^+NHCH_2CH_2COOH$ where $X^-$ is an acid anion selected from the group of acid phosphate, acid fumarate, acid oxalate, acid maleate and/or acid pamoate, orotate, galactarate, sulfate, dichloroacetate, acid galactarate, fumarate, taurate, maleate, acid aspartate, creatinate, acid sulfate, magnesium succinate, acid citrate, citrate, succinate, acid succinate, adipinate, acid tartrate and lactate, which distinguish from 3-(2,2,2-trimethylhydrazinium) propionate dihydrate by low hygroscopicity and/or increased thermal stability and/or lasting action. This invention relates also to the method of such salt preparation and to pharmaceutical formulations containing the said salts.

BACKGROUND OF THE INVENTION 3-(2,2,2-Trimethylhydrazinium) propionate is disclosed in U.S. Pat. No. 4,481,218.

It is well known that 3-(2,2,2-trimethylhydrazinium) propionate as dihydrate (this substance being known under its International Nonproprietary Name of Meldonium) is widely used for controlling carnitine and gamma-butyrobetaine concentration ratio and consequently the speed of fatty acid beta-oxidation in the body (Dambrova M., Liepinsh E., Kalvinsh I. Mildronate: cardioprotective action through carnitine-lowering effect. Review.//Trends Cardiovasc. Med.-2002.-Vol. 12, N.6. -P. 275–279. Rupp H., Zarain-Herzberg A., Maisch B. The use of partial fatty acid oxidation inhibitors for metabolic therapy of angina pectoris and heart failure//Herz, 2002-Vol. 27, N.7.-P. 621–636. Mildronate, Met-88. Drugs Fut. 2001, 26(1), p. 82).

Due to these properties, Meldonium (registered with the trade mark of "MILDRONĀTS®", "MILDRONATE®", "МилдРОНАТ®") is extensively applied in medicine as an anti-ischemic un stress-protective drug in treating various cardio-vascular diseases and other pathologies involving tissue ischemia (R. S. Karpov, O. A. Koshelskaya, A. V. Vrublevsky, A. A. Sokolov, A. T. Teplyakov, I. Skarda, V. Dzerve, D. Klintsare; A. Vitols, I. Kalvinsh, L. Matveyeva, D. Urbane. Clinical efficacy and safety of Mildronate in patients with ischemic heart disease and chronic heart failure. Kardiologiya, 2000, Vol. 6, -P. 69–74.)

However, Meldonium as dihydrate has essential drawbacks, the first of which consists in its rather high hygroscopicity. Already after 24 hours maintenance at 100% air humidity, Meldonium mass is increased by 10% because of water absorption, the substance being transformed into a syrup.

Other essential drawback of Meldonium is caused by the half-elimination period equalling 4–10 hours for humans while this drug must be used 2–4 times daily in the clinic (V. Dzērve. Mildronāts. PAS "Grindeks", 1999, p. 1), though it is longer in trials on rats (K. Yoshisue, Y. Yamomoto, K. Yoshida, M. Saeki, Y. Minami, Y. Esumi, Y. Kawaguchi. Pharmacokinetics and biological fate of 3-(2,2,2-trimethylhydrazinium)propionate (MET-88), a novel cardioprotective agent, in rats. Drug Metabolism and Disposition, vol. 28, No 6, 687–694).

As Meldonium dihydrate is unsuitable for single daily oral introduction, it was one of the aims of the present invention to find other pharmacologically acceptable Meldonium forms which would be applicable for single daily use. It is generally known that amino acid betaine salts usually have good solubility in water. If pharmacologically acceptable acids are selected, resorption and elimination pharmacokinetics and biological activity of these salts normally does not much differ from the parameters of the initial compound.

Besides, Meldonium is not very stable: while heated, it fast loses the water of the crystal hydrate. In turn, the anhydrous form of Meldonium is unstable and extremely hygroscopic. In such form, this compound soon becomes coloured and gets a specific annoying odour. Thus, the hygroscopicity and thermal non-stability of Meldonium dihydrate are significant disadvantages restricting the possibilities of preparing different oral and external drug dosage forms from this compound. Furthermore, Meldonium dihydrate is actively dehydrated at temperatures so low as 40–45° C. This means that sure storage of Meldonium dosage forms containing crystal hydrate is rather embarrassing in countries with hot climate.

Because Meldonium dihydrate is not readily applicable for producing drug oral dosage forms, it was a further object of this invention to find other pharmacologically acceptable salts of Meldonium which would lack hygroscopicity or/and, be thermally stable and could be stored in any climatic zone for a long time.

DETAILED DESCRIPTION OF THE INVENTION

For most Meldonium salts, their pharmacokinetic properties practically do not differ from those described for Meldonium. Therefore the use of these salts for preparing pharmaceutical compositions seemingly have no advantage as compared to Meldonium.

To our surprise, we suddenly found that Meldonium salts of some pharmaceutically acceptable polybasic acids are an exception in this respect; although readily soluble in water, they essentially differ from Meldonium by their pharmacokinetic and pharmacodynamic properties.

It was an astonishing discovery since no theoretical argument exists why Meldonium salts, which are easily soluble in water should have resorption and elimination speed different from that of Meldonium.

Nevertheless, we succeeded in finding among the above salts some specific Meldonium salts with appropriate pharmacokinetics and pharmacodynamics allowing their single daily use; they are: $X^-(CH_3)_3N^+NHCH_2CH_2COOH$ where $X^-$ is the anion of acids is selected from the group of mono-substituted fumaric acid, mono-substituted phosphoric acid, mono-substituted oxalic acid, mono-substituted maleic acid un mono- and/or di-substituted galactaric, pamoic acids and orotic acid.

It is common knowledge that betaines of amino acids are commonly relatively stable substances. It is well known that these compounds are readily soluble in water and the biological activity of their pharmacologically acceptable salts usually does not differ from that of the initial compound.

However, Meldonium and monobasic, dibasic as well as tribasic pharmaceutically acceptable acid salts have equal or even higher hygroscopicity than Meldonium itself. Moreover, many of them cannot be prepared in crystalline form at all because they form syrups containing variable quantity of water.

The salts of both strong and weak acids, viz. Meldonium sulfate, hydrogen chloride, acetate, lactate, citrate as well as salts of many other pharmaceutically acceptable acids are hygroscopic. Consequently, using these salts for preparation of pharmaceutical compositions for oral use is deemed lacking preference to that of Meldonium.

We noticed completely unexpectedly that Meldonium salts of some pharmaceutically acceptable polybasic acids are exceptional in this regard; they proved to be practically non-hygroscopic though easily soluble in water. We observed that these compounds are also very stable while maintained at both room temperature and temperatures up to at least 50 centigrade over a long period of time. Similarly we gained the unanticipitated result that such specific monobasic acid as orotic acid forms a non-hygroscopic Meldonium salt, too. All of the claimed salts proved more stable thermally than Meldonium.

Orally administered Meldonium is easily bioavailable also from these salts, therefore these salts are much more suitable for preparing various drug dosage forms than the hygroscopic and thermally unstable Meldonium. It was an astounding discovery because no theoretical underpinning suggests any difference of Meldonium orotate or polybasic acid salts, which are also readily soluble in water, from other salts as to hygroscopicity.

Since they are not hygroscopic and/or have increased thermal stability, these salts can be easily handled and are favourably suitable for manufacturing solid administration forms. Their aqueous solutions are less acid than those of the corresponding chlorides: consequently these salts are also more suitable for manufacturing injectable administration forms.

The following non-limiting examples illustrate the preparation of salts according to the present invention.

EXAMPLE 1

The following methods may be applied for the preparation of these salts. Meldonium is dissolved in water or other appropriate solvent, an equimolar quantity of a polybasic acid selected from the group of fumaric acid, phosphoric acid, aspartic acid, citric acid, lactic acid, maleic acid, oxalic acid, or orotic acid (the latter is taken in semi-molar quantity) is added, and the mixture is stirred at temperature from 20 to 50° C. till the corresponding salt is formed. At the second technological stage, Meldonium salts are evaporated to dryness if necessary. At the third technological stage, in case of need the obtained salts are recrystallised from a suitable solvent.

EXAMPLE 2

The said salts can also be prepared from the corresponding salts of Meldonium production intermediates, viz. methyl- or ethyl-esters of 3(2,2,2,-trimethylhydrazinium) propionate, the latter being heated together with the corresponding acids in aqueous or aqueous-alcoholic solutions, and subsequent treatment, eduction and purification being performed by analogy with the first method of preparation.

EXAMPLE 3

Method of salt preparation from meldonium dihydrate. Meldonium and the corresponding acid are dissolved in a small quantity of water at 40–50° C. under stirring. The obtained solution is evaporated in vacuum at 40–50° C. Acetone or acetonitrile is added to the formed mass (what predominantly is viscous syrup), and the mixture is grated. The precipitated crystalline mass is stirred in acetone or acetonitrile during several hours, filtered off, washed with acetone or acetonitrile, dried in vacuum at room temperature.

Sample hygroscopicity was tested by $H_2O$ content determination before the test and after 24 hours maintenance at 100% humidity (keeping in a closed vessel over water). On such conditions, Meldonium absorbs 10% water (as to mass increase) during 24 hours. Water content was determined by titration by Fischer's method; in cases of syrup formation water content is determined by sample mass increase.

The claimed invention is illustrated by, but not restricted to the following examples of salts obtained by the above method:

EXAMPLE 4

Meldonium orotate (1:1). Mp. 211–214° C. $^1$H NMR spectrum ($D_2O$), δ, ppm: 2.56 (2H, t, $CH_2COO^-$); 3.29 (2H, t, $CH_2N$); 3.35 (9H, s, $Me_3N^+$); 6.18 (1H, s, —CH=). Found, %: C, 43.78; H, 6.01; N, 18.48. Calculated, %: C, 43.71; H, 6.00; N, 18.53. Initially $H_2O$ content in the sample was 0.3919%; during 24 hours at 100% humidity it remains unchanged.

EXAMPLE 5

Meldonium phosphate (1:1). Mp. 158–160° C. $^1$H NMR spectrum ($D_2O$), δ, ppm: 2.60 (2H, t, $CH_2COO^-$); 3.31 (2H, t, $CH_2N$); 3.35 (9H, s, $Me_3N^+$). Found, %: C, 29.64; H, 7.05; N, 11.33 Calculated, %: C, 29.51; H, 7.02; N, 11.47. Initially $H_2O$ content in the sample was 0.0762%; during 24 hours at 100% humidity it remains unchanged.

EXAMPLE 6

Meldonium fumarate (1:1). Mp. 140–142° C. $^1$H NMR spectrum, δ, ppm: 2.57 (2H, t, $CH_2$); 3.29 (2H, t, $CH_2$); 3.35 (9H, s, $Me_3N^+$); 6.72 (2H, s, —CH=CH—). Found, %: C, 45.46; H, 6.94; N, 10.72. Calculated, %: C, 45.80, H, 6.92; N, 10.68. Initially $H_2O$ content in the sample was 0.18%; during 24 hours at 100% humidity it remains unchanged.

EXAMPLE 7

Meldonium oxalate (1:1). Mp. 123–125° C. $^1$H NMR spectrum ($D_2O$), δ, ppm: 2.61 (2H, t, $CH_2COO^-$); 3.30 (2H, t, $CH_2N$); 3.35 (9H, s, $Me_3N^+$). Found, %: C, 40.86; H, 6.82; N, 11.78 Calculated, %: C, 40.68; H, 6.83; N, 11.86. Initially $H_2O$ content in the sample was 0.1661%; after 24 hours maintenance at 100% humidity it was 3.1211%.

EXAMPLE 8

Meldoniuma maleate (1:1). Mp. 98–100° C. $^1$H NMR spectrum ($D_2O$), δ, ppm: 2.60 (2H, t, $CH_2COO^-$); 3.31 (2H, t, $NCH_2$); 3.35 (9H, s, $Me_3N^+$); 6.35 (2H, s, —CH=CH—). Found, %: C, 45.93; H, 6.95; N, 10.65. Computational, %: C, 45.80; H, 6.92; N, 10.68. Initially $H_2O$ content in the sample was 0.387%; after 24 hours maintenance at 100% humidity it was 4.6844%.

EXAMPLE 9

Meldonium mucate (galactarate; 2:1; $xH_2O$). Mp. 152–154° C. $^1$H NMR spectrum ($D_2O$), δ, ppm: 2.46 (4H, t, 2×CH$_2$COO$^-$); 3.26 (4H, t, 2×NCH$_2$); 3.35 (18H, s, 2×Me$_3$N$^+$); 3.98 un 4.31—two singlets of low intensity, protons of mucic acid. Found, %: C, 42.13; H, 7.58; N, 10.77. Calculated, %: C, 41.53; H, 7.75; N, 10.76. Initially H$_2$O content in the sample was 3.0414%; after 24 hours maintenance at 100% humidity it was 7.6830%.

EXAMPLE 10

Meldonium pamoate (1:1; ×H$_2$O). Meldonium (5.46 g, 30 mmol) and pamoic acid (5.82 g, 15 mmol) are mixed with water and acetone (15+15 ml), the formed suspension is evaporated, 30–40 ml toluene is added to the residual viscous mass, it is grated, and evaporation is repeated. If the residue is insufficiently dry, treatment with toluene is repeated. Mp. 128–133° C. (decomp.). $^1$H NMR spectrum (DMSO-d$_6$), δ, ppm: 2.41 (2H, t, CH$_2$COO$^-$); 3.14 (2H, t, CH$_2$N); 3.25 (9H, s, Me$_3$N$^+$); 4.75 (2H, s, —CH$_2$—$_{(pam.)}$); 7.12 (2H, t, H$_{arom}$); 7.26 (2H, td, H$_{arom}$); 7.77 (2H, d, H$_{arom}$); 8.18 (2H, s, H$_{arom}$); 8.35 (2H, s, H$_{arom}$). Found, %: C, 62.90; H, 5.83; N, 4.98. Calculated, %: C, 63.07; H, 5.84; N, 5.07. Initially H$_2$O content in the sample was 1.71%; after 24 hours maintenance at 100% humidity sample mass increased by 9% due to absorbed water.

EXAMPLE 11

Meldonium sulfate (2:1). T$_m$ 80–182° C. (decomp.). $^1$H NMR spectrum (D$_2$O), δ, ppm: 2.60 (4H, t, 2×CH$_2$COO$^-$); 3.30 (4H, t, 2×CH$_2$N); 3.35 (18H, s, 2×Me$_3$N$^+$). Found, %: C, 37.08; H, 7.73, N, 14.29; S, 8.20. Calculated: %: C, 36.91; H, 7.74; N, 14.35; S, 8.21. Initially H$_2$O content in the sample was 0.313%; after 24 hours maintenance at 100% humidity sample mass increased by 11.8% due to absorbed water.

EXAMPLE 12

Meldonium dichloroacetate (1:1). Mp. 86–88° C. $^1$H NMR spectrum (D$_2$O), δ, ppm: 2.61 (2H, t, CH$_2$COO$^-$); 3.31 (2H, t, CH$_2$N); 3.35 (9H, s, Me$_3$N$^+$); 6.05 (1H, s, —CHCl$_2$). Found, %: C, 35.13; H, 5.85; N, 10.10. Calculated, %: C, 34.92; H, 5.86; N, 10.18. Initially H$_2$O content in the sample was 1.17%; after 24 hours maintenance at 100% humidity sample mass increased by 12% due to absorbed water.

EXAMPLE 13

Meldonium mucate (galactarate; 1:1). Mp. 152–154° C. $^1$H NMR spectrum (D$_2$O), δ, ppm: 2.47 (2H, t, CH$_2$COO$^-$); 3.26 (2H, t, CH$_2$N); 3.35 (9H, s, Me$_3$N$^+$); 3.71 and 3.98—two singlets of low intensity, protons of the slightly soluble mucic acid. Found, %: C, 40.22; H, 6.75; N, 7.75%. Calculated, %: C, 40.22; H, 6.79; N, 7.86. Initially H$_2$O content in the sample was 1.98%; after 24 hours maintenance at 100% humidity it was 12.8%.

EXAMPLE 14

Meldonium fumarate (2:1). Mp. 156–158° C. $^1$H NMR spectrum (D$_2$O), δ, ppm: 2.53 (4H, t, 2×CH$_{2(meld)}$); 3.29 (4H, t, 2×CH$_{2(meld)}$); 3.35 (18H, s, 2×Me$_3$N$^+$); 6.65 (2H, s, —CH=CH—$_{(fum.ac.)}$). Found, %: C, 46.68; H, 7.91; N, 13.69. Calculated, %: C, 47.05; H, 7.90; N, 13.72. Initially H$_2$O content in the sample was 1.5136%; after 24 hours maintenance at 100% humidity it was 13.4707%.

EXAMPLE 15

Meldonium 2-aminoethane sulfonate (taurate; 1:1; ×1.5H$_2$O). Mp. 190–193° C. (with decomp.). $^1$H NMR spectrum (D$_2$O), δ, ppm: 2.38 (2H, t, CH$_2$COO$^-$); 3.18–3.30 (4H, m, NCH$_{2(meld.)}$+CH$_{2(taur.)}$); 3.34 (9H, s, Me$_3$N$^+$); 3.42 (2H, t, CH$_{2(taur.)}$). Found %: C, 32.40; H, 8.16; N, 13.98; S, 10.60. Calculated, %: C, 32.21; H, 8.11; N, 14.08; S, 10.75. Initially H$_2$O content in the sample was 9,4824%; after 24 hours maintenance at 100% humidity it was 17.0854%.

EXAMPLE 16

Meldonium maleate (2:1). Mp. 104–106° C. $^1$H NMR spectrum (D$_2$O), δ, ppm: 2.54 (4H, t, CH$_2$COO$^-$); 3.30 (4H, t, CH$_2$N); 3.35 (18H, s, Me$_3$N$^+$); 6.42 (2H, s, —CH=CH—). Found, %: C, 46.59; H, 7.88; N, 13.50. Calculated: C, 47.05; H, 7.90; N, 13.72. Initially H$_2$O content in the sample was 1.3595%; after 24 hours maintenance at 100% humidity sample mass increased by 18% due to absorbed water.

EXAMPLE 17

Meldonium L-(+)-aspartate (1:1; ×2H$_2$O). Mp. 146–148° C. $^1$H NMR spectrum (D$_2$O), δ, ppm: 2.49 (2H, t, CH$_2$COO$^-$); 2.70–2.99 (2H, m, CH$_{2(asp.)}$) 3.27 (2H, t, CH$_2$N); 3.35 (9H, s, Me$_3$N$^+$); 3.95 (1H, dd, CHNH$_2$). Found, %: C, 37.71; H, 7.85; N, 13.03. Calculated, %: C, 38.09; H, 7.99; N, 13.33. Initially H$_2$O content in the sample was 12.5%; after 24 hours maintenance at 100% humidity sample mass increased by 18% due to absorbed water.

EXAMPLE 18

Meldonium creatinate (1:1; ×3H$_2$O). Mp. 227–228° C. (decomp.). $^1$H NMR spectrum (D$_2$O), δ, ppm: 2.38 (2H, t, CH$_2$COO$^-$); 3.03 (3H, s, NMe$_{(creatine)}$); 3.22 (2H, t, CH$_2$N); 3.35 (9H, s, Me$_3$N$^+$); 3.92 (2H, s, NCH$_{2(creatine)}$). Initially H$_2$O content in the sample was 15.8%; after 24 hours maintenance at 100% humidity sample mass increased by 18% due to absorbed water.

EXAMPLE 19

Meldonium sulfate (1:1). T$_m$ 98–100° C. $^1$H NMR spectrum (D$_2$O), δ, ppm: 2.62 (2H, t, CH$_2$COO$^-$); 3.31 (2H, t, CH$_2$N); 3.35 (9H, s, Me$_3$N$^+$). Found, % C: C, 29.23; H, 6.57; N, 11.17; S, 13.10. Calculated: C, 29.50; H, 6.60; N, 11.47; S, 13.13. Initially H$_2$O content in the sample was 1.4189%; after 24 hours maintenance at 100% humidity sample mass increased by 20% due to absorbed water.

EXAMPLE 20

Meldonium magnesium succinate (1:1:1; ×2H$_2$O). (see Meldonium-magnesium tartrate). Mp. 135–140° C. (decomp.). $^1$H NMR spectrum (D$_2$O), δ, ppm: 2.39 (2H, t, CH$_2$COO$^-$); 2.46 (4H, s, —CH$_2$—CH$_2$—$_{(succin.ac.)}$); 3.22 (2H, t, CH$_2$N); 3.35 (9H, s, Me$_3$N$^+$). Found, %: C, 36.66; H, 7.28; N, 8.37. Calculated: C, 37.23; H, 6.87; N, 8.68. Initially H$_2$O content in the sample was 10.1215%; after 24 hours maintenance at 100% humidity sample mass increased by 20% due to absorbed water.

EXAMPLE 21

Meldonium magnesium citrate (1:1:1; ×2H$_2$O) (see Meldonium-magnesium tartrate). Mp. 195–200° C. (decomp.). $^1$H NMR spectrum (D$_2$O), δ, ppm: 2.48 (2H, t, CH$_2$COO$^-$); 2.75 (4H, dd, 2×CH$_{2(citr.)}$); 3.26 (2H, t, CH$_2$N); 3.34 (9H, s, Me$_3$N$^+$). Found, %: C, 36.58; H, 6.09; N, 6.96. Calculated: C, 36.34; H, 6.10; N, 7.06. Initially H$_2$O content in the sample was 9.45%; after 24 hours maintenance at 100% humidity the sample diffused.

EXAMPLE 22

Meldonium citrate (1:1). Mp. 90–95° C. (decomp.). $^1$H NMR spectrum (D$_2$O), δ, ppm: 2.56 (2H, t, CH$_2$COO$^-$); 2.85 (4H, dd, 2×CH$_{2(citr.)}$); 3.28 (2H, t, CH$_2$N); 3.35 (9H, s, Me$_3$N$^+$).

EXAMPLE 23

Meldonium citrate (2:1). Mp. 101–107° C. (decomp.). $^1$H NMR spectrum (D$_2$O), δ, ppm: 2.51 (4H, t, 2×CH$_2$COO$^-$); 2.81 (4H, dd, 2×CH$_{2(Citr.)}$); 3.26 (4H, t, 2×CH$_2$N); 3.35 (18H, s, 2×Me$_3$N$^+$).

EXAMPLE 24

Meldonium succinate (1:1). Mp. 95–100° C. (decomp.). $^1$H NMR spectrum (D$_2$O), δ, ppm: 2.51 (2H, t, CH$_{2(meldon.)}$); 2.60 (4H, s, —CH$_2$—CH$_2$—$_{(succin.ac.)}$); 3.27 (2H, t, CH$_{2(meldon.)}$); 3.35 (9H, s, Me$_3$N$^+$).

EXAMPLE 25

Meldonium succinate (2:1). Mp. 103–107° C. (decomp.). $^1$H NMR spectrum (D$_2$O), δ, ppm: 2.47 (4H, t, 2×CH$_{2(meldon.)}$); 2.59 (4H, s, —CH$_2$—CH$_2$—$_{(succin.ac.)}$); 3.29 (4H, t, 2×CH$_{2(meldon.)}$); 3.35 (18H, s, 2×Me$_3$N$^-$).).

EXAMPLE 26

Meldonium adipinate (2:1). Mp. 110–114° C. (decomp.). $^1$H NMR spectrum (D$_2$O), δ, ppm: 1.55–1.70 (4H, m, 2×CH$_{2(adip.)}$); 2.28–2.39 (4H, m, 2×CH$_{2(adip.)}$); 2.45 (4H, t, 2×CH$_{2(meldon.)}$); 3.24 (4H, t, 2×CH$_{2(meldon.)}$); 3.34 (18H, s, 2×Me$_3$N$^+$).

EXAMPLE 27

Meldonium tartrate (1:1). Mp. 100–107° C. (decomp.). $^1$H NMR spectrum (D$_2$O), δ, ppm: 2.57 (2H, t, CH$_2$COO$^-$); 3.29 (2H, t, CH$_{2(meldon.)}$); 3.35 (9H, s, Me$_3$N$^+$); 4.55 (2H, s, CH$_{(tart.ac.)}$).

EXAMPLE 28

Meldonium lactate (1:1). Mp. 110–114° C. (decomp.). $^1$H NMR spectrum (D$_2$O), δ, ppm: 1.33–1.48 (3H, m, Me$_{(lac.ac.)}$); 2.50 (2H, t, CH$_2$COO$^-$); 3.26 (2H, t, CH$_{2(mildr.)}$); 3.35 (9H, s, Me$_3$N$^+$); 4.21 (1H, q, CH$_{(lac.ac.)}$).

This invention relates also to pharmaceutical formulations containing at least one of the Meldonium salts described herein as pharmaceutical active and pharmaceutically acceptable solid or liquid excipients used in drug dosage form production. Solid formulations suitable for producing dosage forms of oral introduction as well as syrups and solutions containing the claimed salts and excipients are preferable.

In case when the active substance(s) is (are) inserted into tablets, caplets, pills, granules, powders, or capsules, they shall contain a Meldonium salt from 0,5 to 5 gr. per tablet, caplet, pill, capsule or one portion of powder or granules.

The following non-limiting examples illustrate the pharmaceutical formulation of salts for solid formulation

EXAMPLE 29

Formulation for Manufacturing Tablets

| A Meldonium salt according to the invention | 500 mg |
| --- | --- |
| Starch | 20 mg |
| Talc | 10 mg |
| Ca-stearate | 1 mg |
| Total | 531 mg |

The following non-limiting examples illustrate composition suitable for producing capsules is the following:

EXAMPLE 30

| A Meldonium salt according to the invention | 500 mg |
| --- | --- |
| Starch | 66 mg |
| Talc | 26 mg |
| Ca-stearate | 3 mg |
| Total | 602 mg |

In case if the active(s) are introduced by injections or orally by means of drops, a syrup or beverage, the pharmaceutical formulation shall contain a Meldonium salt according to this invention in a ratio of 0,5 to 60% by weight and a pharmaceutically admissible solvent, e.g. distilled water, an isotonic, glucose or buffer solution or mixtures of them.

The following non-limiting examples illustrate the pharmaceutical formulation of salts for injectable administration or/and orally administration:

EXAMPLE 31

Injection Formulation:

| A Meldonium salt according to the invention | 500 mg |
| --- | --- |
| Water for injections | 5 ml |

EXAMPLE 32

A Syrup Formulation:

| A Meldonium salt according to the invention | 25.00 mg |
| --- | --- |
| Methyl-p-hydroxybenzoate | 0.20–0.60 g |
| Propyl-p-hydroxybenzoate | 0.01–0.1 g |
| Propylene glycol | 6.15–8.30 g |
| Sorbit | 120.00–150.50 g |
| Glycerine | 10.00–15.00 g |

-continued

| | |
|---|---|
| Purified water | 108 ml |
| Total | 250 ml |

In case of trans-dermal application of the active(s), it's (their) content in an cream, gel, solution, ointment or plaster shall be 0.5–40% by weight.

The following non-limiting examples illustrate the pharmaceutical formulation of salts for trans-dermal (local/topical) administration:

EXAMPLE 33

Gel Formulation:

| | |
|---|---|
| A Meldonium salt according to the invention | 10.00% |
| Sodium starch glycollate type C, | 4.00 |
| Propylene glycol | 2.00 |
| Fumaric acid | 0.40 |
| Purified vater | 83.40 |

In the case the salt are administered rectally their content in a suppository or microenema accounts for 0.5 to 40% by weight.

The invention claimed is:

1. A meldonium salt selected from those of general formula:

X(CH$_3$)$_3$N$^+$NHCH$_2$CH$_2$COOH wherein X$^-$ is an anion selected from dihydrogen phosphate, hydrogen fumarate, hydrogen oxalate, hydrogen maleate, hydrogen pamoate, orotate, galactarate, sulfate, dichloroacetate, hydrogen galactarate, fumarate, taurate, maleate, hydrogen aspartate, creatinate, hydrogen sulfate, magnesium succinate, hydrogen citrate, citrate, succinate, hydrogen succinate, adipinate, hydrogen tartrate, and lactate anions.

2. A salt of claim 1, which is meldonium dihydrogen phosphate.

3. A salt of claim 1, which is meldonium hydrogen fumarate.

4. A salt of claim 1, which is meldonium orotate.

5. A process for producing a meldonium salt of claim 1, comprising:
  (a) dissolving meldonium having the formula (CH$_3$)$_3$NNHCH$_2$CH$_2$COOH in water or another appropriate solvent;
  (b) adding an equimolar quantity of a polybasic acid selected from fumaric acid, phosphoric acid, aspartic acid, citric acid, lactic acid, maleic acid, oxalic acid, and orotic acid;
  (c) stirring the mixture at a temperature of from 20 to 50° C. until the corresponding salt is formed; and
  (d) evaporating the meldonium salt formed in step (c) to dryness, if necessary; and, optionally, recrystallizing the meldonium salt from a suitable solvent.

6. A pharmaceutical composition for oral or sublingual administration, comprising as active ingredient a salt of claim 1, together with one or more pharmaceutically acceptable carries, wherein the composition is in a solid or liquid form selected from a tablet, with or without coating, a capsule, a caplet, dragees, granules, a powder, a solution, and a syrup, wherein the composition contains from 0.5 to 5 g of the active ingredient in every tablet, capsule, dragee, granule or powder dose, or from 0.5–40% by weight of the active ingredient in a solution or syrup dose.

7. The pharmaceutical composition of claim 6, wherein the pharmaceutically acceptable carrier is selected from one or more of the following: stearic acid and its salts, lactose, glucose, saccharose, starch, talc, vegetable oils, polyethylene glycols, microcrystalline cellulose, aerosil, aromatizers, flavoring agents, colorants, ethyl alcohol, and water.

8. A pharmaceutical composition for parenteral administration, comprising as active ingredient a salt of claim 1, together with a pharmaceutically acceptable solvent, wherein the composition is in the form of a solution for injection, and wherein the composition contains from 0.5 to 40% by weight of the active ingredient.

9. The pharmaceutical composition of claim 8, wherein the pharmaceutically acceptable solvent is selected from one or more of the following: distilled water, isotonic solution, buffer solution, and glucose solution.

10. A pharmaceutical composition for transcutaneous administration comprising as active ingredient a salt of claim 1, together with a pharmaceutically acceptable carrier, wherein the composition is in the form of an ointment, cream, gel, solution or plaster, and wherein the composition contains from 0.5 to 40% by weight of the active ingredient.

11. The pharmaceutical composition of claim 10, wherein the pharmaceutically acceptable carrier is selected from one or more of the following: water, polyethylene glycols 400, 1500 and 4000, vegetable oils, fats, glycerine, preservants, emulgators, stabilizers, porous polymer material, dimethylsulphoxide, alcohol, and water.

12. A pharmaceutical composition for rectal administration comprising as active ingredient a salt of claim 1, together with a pharmaceutically acceptable carrier, wherein the composition is in the form of a suppository or microenema, and wherein the composition contains from 0.5 to 40% by weight of the active ingredient.

13. The pharmaceutical composition of claim 12, wherein the pharmaceutically acceptable carrier is selected from one or more of the following: water, polyethylene glycols 400, 1500 and 4000, vegetable oils, fats, glycerine, preservants, emulgators, and stabilizers.

14. A pharmaceutical composition suitable for once per day administration, comprising as active ingredient a salt of claim 1 together with one or more pharmaceutically acceptable carriers.

* * * * *

UNITED STATES PATENT AND TRADEMARK OFFICE
CERTIFICATE OF CORRECTION

PATENT NO.         : 7,223,797 B2
APPLICATION NO. : 10/567130
DATED              : May 29, 2007
INVENTOR(S)        : Ivars Kalvinsh et al.

It is certified that error appears in the above-identified patent and that said Letters Patent is hereby corrected as shown below:

Line 12 of the Abstract:     Remove one of the "and/or".

Column 9, Line 34:    "$X(CH_3)_3N^+NHCH_2CH_2COOH$" should be
-- $X^-(CH_3)_3N^+NHCH_2CH_2COOH$ --.

Signed and Sealed this

Eleventh Day of December, 2007

JON W. DUDAS
*Director of the United States Patent and Trademark Office*